US00PP26016P3

(12) United States Plant Patent
Olesen

(10) Patent No.: US PP26,016 P3
(45) Date of Patent: Oct. 27, 2015

(54) MINIATURE ROSE PLANT NAMED 'POULPAR078'

(50) Latin Name: ***Rosa* hybrid**
Varietal Denomination: Poulpar078

(71) Applicant: Mogens Nyegaard Olesen, Fredensborg (CK)

(72) Inventor: Mogens Nyegaard Olesen, Fredensborg (CK)

(73) Assignee: Poulsen Roser A/S, Fredensborg (DK)

( * ) Notice: Subject to any disclaimer, the term of this patent is extended or adjusted under 35 U.S.C. 154(b) by 168 days.

(21) Appl. No.: 13/986,928

(22) Filed: Jun. 14, 2013

(65) Prior Publication Data

US 2014/0373206 P1 Dec. 18, 2014

(51) Int. Cl.
*A01H 5/00* (2006.01)

(52) U.S. Cl.
USPC ..... Plt./117

(58) Field of Classification Search
USPC ..... Plt./117, 116
CPC ..... A01H 5/0222; A01H 5/0216; A01H 5/02; A01H 5/00
See application file for complete search history.

(56) References Cited

PUBLICATIONS

Poulsen Roser A/S Kaija retrieved on Jan. 8, 2015, retrieved from the internet <www.poulsenroser.com/assortment/rose-collections/parade/kaija.aspx> one page.*
Upov Pluto Plant Variety Database 20150114 retrieved on Jan. 14, 2015, retrieved from the Internet <www3.wipo.int/pluto/user/en/index.jsp> for *Rosa* Poulpar078 one page.*

* cited by examiner

*Primary Examiner* — June Hwu

(57) ABSTRACT

A new miniature rose plant that has abundant, white flowers and attractive foliage. The variety successfully propagates from softwood cuttings and is suitable for year-round production in commercial glasshouses. This new and distinct variety has shown to be uniform and stable in the resulting generations from asexual propagation.

1 Drawing Sheet

Botanical designation: *Rosa* hybrid.
Variety denomination: 'Poulpar078'.

SUMMARY OF THE INVENTION

The present invention constitutes a new and distinct variety of miniature rose plant which originated from a controlled crossing between the female seed parent, an unnamed seedling, and the male pollen parent, also an unnamed seedling.

The two parents were crossed during the summer of 2007 and the resulting seeds were planted in a controlled environment in Fredensborg, Denmark. The new variety, named 'Poulpar078', originated as a single seedling from the stated cross.

The new variety may be distinguished from its male pollen parent and female seed parent primarily by flower coloration and growth habit.

The objective of the hybridization of this rose variety for commercial culture was to create a new and distinct variety with unique qualities, such as:

1. Uniform and abundant white flowers;
2. Vigorous and compact growth;
3. Year-round flowering under glasshouse conditions;
4. Suitability for production from softwood cuttings in pots;
5. Durable flowers and foliage which make a variety suitable for distribution in the floral industry.

This combination of qualities is not present in previously available commercial cultivars of this type, known to the inventor, and distinguish 'Poulpar078' from all other varieties of which we are aware.

As part of the rose development program, Mogens N. Olesen germinated the seeds from the aforementioned hybridization and conducted evaluations on the resulting seedlings in a controlled environment in Fredensborg, Denmark. 'Poulpar078' was selected by the inventor as a single plant from the progeny of the hybridization in 2007.

Asexual reproduction of 'Poulpar078' by vegetative stem cuttings was first done by Mogens N. Olesen in the nursery in Fredensborg, Denmark in 2008. This initial and other subsequent propagations conducted in controlled environments have demonstrated that the characteristics of 'Poulpar078' are true to type and are transmitted from one generation to the next.

DESCRIPTION OF THE DRAWING

The accompanying color illustration shows as true as is reasonably possible to obtain in color photographs of this type, the typical characteristics of the buds, flowers, leaves, and stems, of 'Poulpar078'. Specifically illustrated in the drawing are flowers at various stages of development, flower in parts, leaves, and stems.

DETAILED DESCRIPTION OF THE VARIETY

The following is a description of 'Poulpar078', as observed in its growth in glasshouses in Burlington, Ontario. Observed plants are 3 months of age and were cultivated in 10.5 cm pots. Color references are made using The Royal Horticultural Society (London, England) Colour Chart, 2001, except where common terms of color are used.

For a comparison, several physical characteristics of the rose variety 'Poulra022', U.S. Plant Pat. No. 15,142 are compared to 'Poulpar078' in Chart 1.

CHART 1

| | 'Poulpar078' | 'Poulra022' |
|---|---|---|
| Petalage: | 75 petals total, 15 of which are petaloids | 70 |
| Flower Diameter: | 55 mm | 35 to 40 mm |
| General Tonality of Flower Color: | White Group 155C with intonations of Green-White Group 157A | Yellow-White Group 158D |

FLOWER AND FLOWER BUD

Blooming habit: Continuous.

Flower bud:

*Size.*—Upon opening, 23 mm in length from base of receptacle to end of bud. 12 mm in diameter.

*Bud form.*—Ovate.

*Bud color.*—As sepals unfold, petals are Green-White Group 157D.

*Sepals.*—Upper Surface: Color: Green Group 138C. Texture: Smooth and pubescent. Lower Surface: Color: Yellow Green Group 144A. Texture: Smooth. Shape: Apex: Cirrhose. Base: Flat at union with receptacle. Margins: Margins have moderate foliaceous appendages on three of the five sepals. Size: 25 to 35 mm long by 8 mm wide.

*Receptacle.*—Surface Texture: Smooth. Shape: Broad funnel. Size: 5 mm tall and 9 mm wide. Color: Yellow Green Group 144A.

*Pedicel.*—Surface: Somewhat rough with stipitate glands. Length: 15 to 35 mm. Diameter: Generally 2.5 mm. Color: Yellow-Green Group 144A. Strength: Strong.

*Borne.*—Singly.

Flower bloom:

*Fragrance.*—Light floral scent.

*Duration.*—As a pot plant, flowers last up to 28 days.

*Size.*—Flower diameter is 55 mm when open. Flower depth is 25 mm.

*Form.*—General shape is a hybrid tea with a high pointed center. Fully opened flowers are globose.

*Shape of flower, side view.*—The upper portion convex. The lower portion is concave.

*Flower type.*—Double.

Petalage: On average flowers have 75 petals total, 15 of which are petaloids.

Color:

*General tonality.*—On open flower White Group 155C with intonations of Green-White Group 157A.

*Upon opening, petals.*—Outermost petals are Green-White Group 157D on the upper surface. Green-White Group 157D on the lower surface with intonations of Yellow-Green Group 149D. Innermost petals are Green-White Group 157D on the upper surface. Green-White Group 157D on the lower surface. Occasionally, there are small basal petal spots the color of Yellow-Green Group 150D on the upper and lower surface of the innermost petals.

*After opening, petals.*—Outermost petals are Green-White Group 157D on the upper surface. Green-White Group 157D on the lower surface with intonations of Yellow-Green Group 149D. Innermost petals are Green-White Group 157D on the upper surface. Green-White Group 157D on the lower surface. Occasionally, there are small basal petal spots the color of Yellow-Green Group 150D on the upper and lower surface of the innermost petals.

Petals:

*Petal reflex.*—Strong.

*Margin.*—Entire, with strong undulations.

*Shape.*—Generally rounded. Apex shape: Rounded. Base shape: Rounded.

*Size.*—23 mm (l) by 28 mm (w).

*Texture.*—Smooth.

*Thickness.*—Average.

Petaloids:

*Quantity.*—15 on average.

*Shape.*—The apex and base are acute.

*Color.*—Yellow-Green Group 150D on the upper and lower surface.

*Size.*—8 mm (l) by 6 mm (w).

Reproductive organs:

*Pollen.*—None Observed.

*Anthers.*—Size: 1 mm long. Color: Yellow Group 11A. Quantity: 25 on average.

*Filaments.*—Color: Green-White Group 157A. Length: About 3 mm.

*Pistils.*—Length: About 4 mm long. Quantity: 15 on average.

*Stigmas.*—Superior relative to the length of the filaments and the height of the anthers. Color: Yellow-Green Group 149D.

*Styles.*—Color: Yellow-Green Group 149D.

*Seed formation.*—Not observed.

PLANT

Plant growth: Upright. Plants are about 17 cm in height, and 15 cm wide.

Stems:

*Color.*—Juvenile growth: Yellow-Green Group 144A. Mature growth: Yellow-Green Group 146A.

*Length.*—Canes are about 11 cm from the base of the plant to the flowering portion.

*Diameter.*—3 mm.

*Internodes.*—On mature canes, there is an average distance of 20 mm between nodes.

*Surface texture.*—Young and mature wood is smooth.

Prickles: None observed.

Plant foliage:

*Compound leaf size.*—65 mm (l) by 50 mm (w).

*Quantity.*—4 leaves per 10 cm of stem.

*Leaf bearing angle to stem.*—90 degrees.

*Color of juvenile foliage.*—Upper Leaf Surface: Yellow-Green Group 144A. Lower Leaf Surface: Yellow-Green Group 144B.

*Color of mature foliage.*—Upper Leaf Surface: Yellow-Green Group 147A. Lower Leaf Surface: Yellow-Green Group 147B.

Plant leaves and leaflets:

*Stipules.*—Size: About 6 mm in length. Shape: Linear, slightly broad based with outward extending apecies.

Margins: Finely serrated with few stipitate glands. Color: Yellow-Green Group 146B.

*Petiole*.—Length: 16 mm on average. Diameter: About 2 mm. Upper surface: Yellow-Green Group 146B. Lower surface: Yellow-Green Group 144B.

*Rachis*.—Length: 18 mm on average. Diameter: About 2 mm. Upper surface: Yellow-Green Group 146B. Lower surface: Yellow-Green Group 144B.

*Leaflet*.—Number of leaflets: 5 on normal leaves in middle of the stem. Size: 35 mm in length by 20 mm wide. Margin: Serrate. General Shape: Elliptical. Apex Shape: Acute. Base Shape: Slightly attenuate to rounded. Texture: Smooth. Arrangement: Odd pinnate. Venation: Reticulate. Leaf Gloss: Moderately glossy.

Cold hardiness: The variety is tolerant to USDA Cold Hardiness Zone 6.

Heat tolerance: The variety has been found to be suitable for climate conditions found in the American Horticulture Society heat zone 7.

Disease resistance: Above average resistance to powdery mildew *Sphaerotheca pannosa*, downy mildew *Peronospora sparsa*, rust *Phragmidium* sps., black spot *Diplocarpon rosae*, and *Botrytis cinerea* under normal growing conditions.

The invention claimed is:

1. A new and distinct variety of rose plant of the miniature class named 'Poulpar078', substantially as illustrated and described herein, due to its abundant, white flowers, vigorous growth, compact habit, suitability for production from softwood cuttings in pots, and durable flowers and foliage that make the variety suitable for distribution in the floral industry.

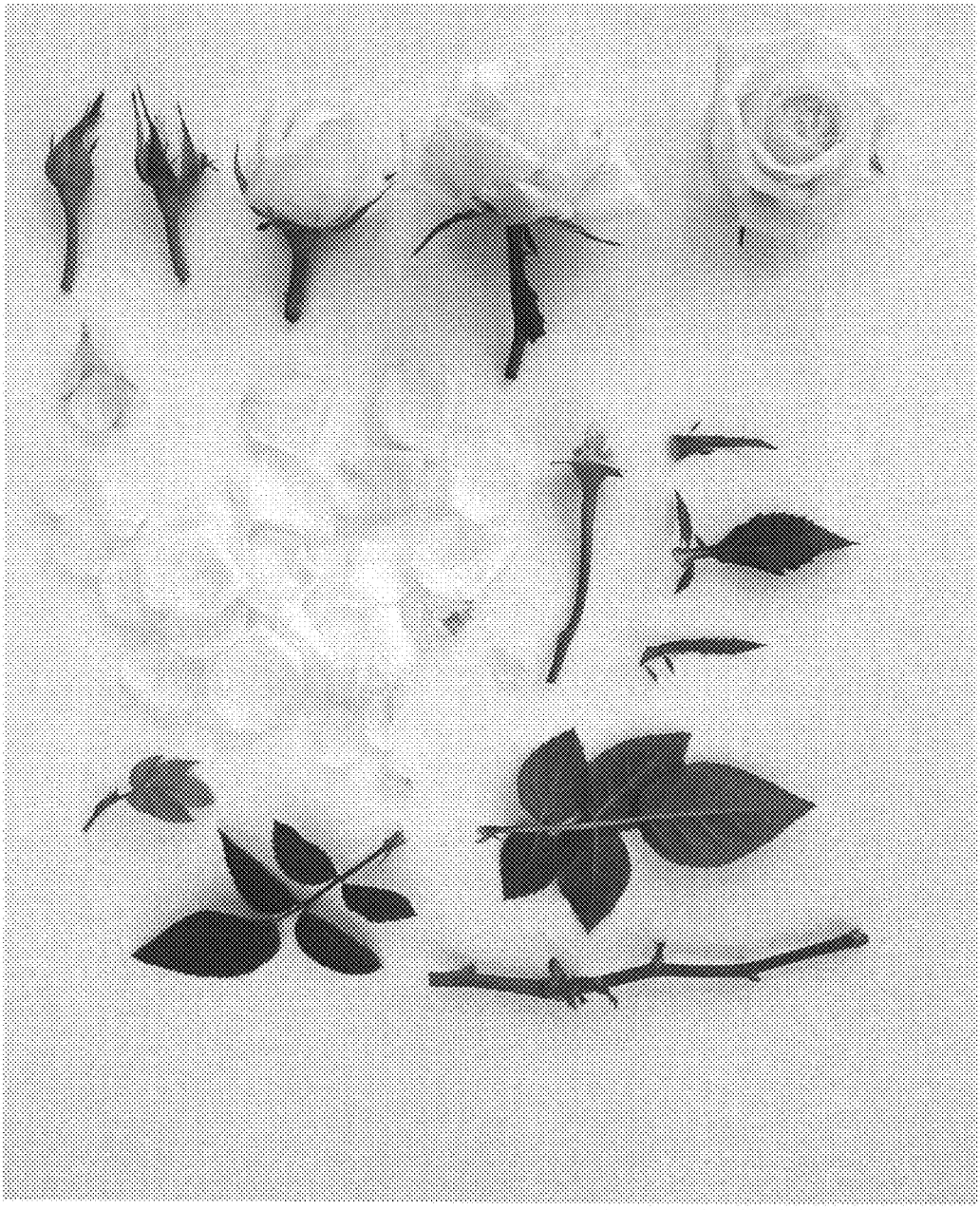

* * * * *